United States Patent [19]
Tal

[11] Patent Number: 4,975,969
[45] Date of Patent: Dec. 4, 1990

[54] METHOD AND APPARATUS FOR UNIQUELY IDENTIFYING INDIVIDUALS BY PARTICULAR PHYSICAL CHARACTERISTICS AND SECURITY SYSTEM UTILIZING THE SAME

[75] Inventor: Peter Tal, 53 Driftwood Dr., Port Washington, N.Y. 11050

[73] Assignee: Peter Tal, Port Washington, N.Y.

[21] Appl. No.: 112,380

[22] Filed: Oct. 22, 1987

[51] Int. Cl.$^5$ .............................................. G06K 9/00
[52] U.S. Cl. .......................................... 382/2; 382/5; 340/825.33; 340/825.34; 364/413.02
[58] Field of Search .................. 382/2, 5; 340/825.34, 340/825.33; 364/413.02; 73/629; 128/660, 774

[56] References Cited

U.S. PATENT DOCUMENTS

| | | | |
|---|---|---|---|
| 3,805,238 | 4/1974 | Rothfjell | 382/2 |
| 4,135,147 | 1/1979 | Riganati et al. | 382/5 |
| 4,154,114 | 5/1979 | Katz et al. | 364/413.02 |
| 4,386,266 | 5/1983 | Chesarek | 340/825.3 |
| 4,729,128 | 3/1988 | Grimes et al. | 340/825.34 |

OTHER PUBLICATIONS

"The Representation and Matching of Pictorial Structures" by Martin A. Fischler and Robert A. Elschlager, *IEEE Transaction on Computers*, Jan. 1973.
"Multivariated Data Representation and Analysis by Face Pattern Using Facial Expression Characteristics" by Nakaji Honda, *Pattern Recognition*, vol. 19, No. 1, pp. 85-94, 1986.
"Machine Identification of Human Faces" by Harmon et al., *Pattern Recognition*, vol. 13, No. 2, 97-110, 1981.

*Primary Examiner*—Leo H. Boudreau
*Assistant Examiner*—Yon Jung
*Attorney, Agent, or Firm*—David P. Gordon

[57] ABSTRACT

Method, apparatus and security system for uniquely identifying individual by their particular physical characteristics are provided. In particular, facial parameters which are defined as being the distances between identifiable points on the human face, and/or ratios of the facial parameters can be used to identify an individual as the parameters for each individual are unique. Thus, by coding the parameter and/or parameter ratio information of an individual on a card, and by scanning the face of the presenter of that card to obtain parameter and/or parameter ratio information of the presenter, a determination can be made as to whether the presenter is that individual whose information is on the card. Particular parameters such as the distance between the eye retinae, the distance from each eye retinae to the nose bottom and to the mouth center, and the distance from the nose bottom to the mouth center are set forth, as they may be particularly defined due to the shadowed definable points at each end.

63 Claims, 4 Drawing Sheets

METHOD AND APPARATUS FOR UNIQUELY IDENTIFYING INDIVIDUALS BY PARTICULAR PHYSICAL CHARACTERISTICS AND SECURITY SYSTEM UTILIZING THE SAME

BACKGROUND

The present invention relates to a method and apparatus for uniquely identifying individuals and security systems and which rely upon such an identification. More particularly, the invention relates to a method and apparatus for uniquely identifying an individual by obtaining and characterizing unique physical characteristics of the individual.

Identification systems and methods are well known in the art and fall into different classifications. One group of systems and methods involves the finger prints and/or palm prints of individuals which are believed to be unique to an individual. Examples of these systems and methods may be had with reference to (among others) U.S. Pat. Nos. 4,636,622 to Clark, 4,582,985 to Lofberg, 4,253,086 to Szwarcbier, 4,246,568 to Paterson, 4,186,378 to Moulton, 3,648,240 to Jacoby et al., and 3,581,282 to Altman. Another set of indentification systems and methods involve the "signature" of an individual, whether it be the written signature or a voice "signature". Examples of these systems and methods may be had by reference to (among others) U.S. Pat. Nos. 4,653,107 to Shojima et al., 4,281,313 to Boldbridge, 4,078,226 to EerNisse at al., 3,896,266 to Waterbury, 3,621,720 to Clark, and 3,412,493 to French.

Yet another identification system known in the art is to use the facial curves of an individual to establish identification. The facial curve method is seen in U.S. Pat. No. 3,805,238 to Rothfjell where the facial curves (two or three dimensional) of an individual taken from full-face, forty-five degree angle, and profile (ninety degree angle) photographs may be defined and stored on an identity card or in a data processing machine. Identification of the individual may be had by first visually comparing the photographs on the identity card to the individual presenting the card, and then, if desired, taking an image of the individual and automatically comparing by computer the curves stored on the identity card with curves derived from the image. In order to properly compare such an image with the computer data, however, the individual must be positioned and aligned in front of a glass screen.

Those skilled in the art will appreciate that security systems typically rely on the positive identification of an individual. One group of security systems relies on identification information contained on plastic cards (apparatus). Examples of the same may be had by reference to U.S. Pat. Nos. 4,528,442 to Endo, 4,636,622 to Clark, 4,476,468 to Goldman, 3,806,704 to Shinal, and 3,639,905 to Yaida et al. The information may be stored on the cards in an optical form such as is disclosed in U.S. Pat. Nos. 4,500,777, 4,542,288, and 4,544,835 to Drexler, or magnetically stored such as is well known in the arts. Other manners of storing information on cards include laminating a bar code to the card such that it may read optically, punching holes in the cards such as was standard in the early computer arts, and implanting actual silicon-type memory devices (such as for example an EEPROM) into the card. Indeed, many bank cards and credit cards in use today store identification information in some of those manners.

While the identification apparatus and methods of the art and the security systems utilizing such identifications provide various degrees of protection, they all suffer from different shortcomings. For example, systems which utilize cards which store personal data, and which require the user to provide the data which may then be compared to the stored data may be compromised in several manners. First, an "intruder" may obtain the personal data, and then may counterfeit a card which would then contain the personal ID of the true card owner. Second, an "intruder" may obtain (e.g. through larceny) the card and the personal data of the card owner. Systems which attempt to circumvent the above-listed shortcomings by comparing information obtained from a user of a card upon use of the card with information stored on the card have other shortcomings. Systems which would require the user to submit to fingerprinting suffer from the difficulties in and the computational requirements of comparing two sets of fingerprints. Moreover, if the security system is to be used by the public at large, the psychological aspects of subjecting an individual to fingerprinting on a regular basis would have to be considered. Also, systems depending on signature comparisons are subject to inaccuracy difficulties such as false acceptance (such as due to forgery), and false rejections. Further yet, almost all security or transaction approval systems presently available are limited to on-line operation and are limited to a certain number of cardholder members that the system will accept. With these systems, the more complex the data contained on the card, the longer becomes the access and processing time. Likewise, it will be appreciated that as the number of users of a typical system increases, the system speed decreases.

Because the shortcomings of the systems and methods of the art, the financial institutions around the globe lose hundreds of millions of dollars annually to fraud. Thus, a fool-proof (intruder-proof) identification system which is practicable from the stand-points of required computation (length of time to establish identity), reliability, and user subjectivity, would be greatly desireable.

SUMMARY OF THE INVENTION

It is therefore an object of the invention to provide an apparatus and method for positively and uniquely identifying an individual.

It is a further object of the invention to provide an apparatus and method for uniquely identifying individuals without requiring them to undergo tests which they can perceive.

It is another object of the invention to provide a fully secure real time security system which utilizes an identification card apparatus containing unique features of the card's owner.

Yet another object of the invention to provide a fully secure security system utilizing an identification card which has very limited storage capacity.

It is even another object of the invention is to provide a security system utilizing a fully secure real time identification system and method which may be utilized in an off-line mode.

In accord with the objects of the invention, the method invention for uniquely identifying an individual generally comprises:

(a) via imaging at least a portion of said individual's head, obtaining at least one ratio of at least a first and second facial parameter of said individual, said first facial parameter comprising the distance from a first identifiable location to a second identifiable location on the individual's head, and said second facial parameter comprising the distance from a third location on the individual's head to one of said first, said second, and a fourth location on the individual's head;

(b) storing values of said at least said ratio of said first and second facial parameters of said individual on a storage medium; and (c) upon attempting to identify an individual requesting access to a secure system, obtaining at least one ratio of first and second facial parameters of said individual requesting access, said ratio corresponding to at least said ratio stored on said storage medium, and comparing the value of said stored ratio with the value of said ratio obtained of said individual requesting access.

It will be appreciated that the preferred apparatus of the invention is closely tied to the preferred method and comprises a card which can store the particular information identified in carrying out the method.

The preferred facial parameters used in the preferred ratios include: the distance between eye retina centers (LER); the distance between the left eye retina center and the mouth center (LEM); the distance between the left eye retina center and the nose bottom (LEN); the distance between the right eye retina center and the mouth center (REM); the distance between the right eye retina center and the nose bottom (REN); and the distance between the mouth center and the nose bottom (DMN). The preferred five ratios include each of the above-listed facial parameters (other than LER) devided by the distance between the eye retina centers. Also, preferably, ratio averages such as (LEN/LER+REN/LER)/2 and (LEM/LER+REM/LER)/2 may be used as parameter ratios. If desired, other facial parameters such as the eye ball ends, the ear tips, etc. may be used, as well as other ratios. Also, if desired, facial parameters obtained from a profile view of an individual may be obtained instead of or to supplement the facial parameters obtained from a frontal view. Likewise, parameter values, or other information particular to a ID card user (a code number; a Social Security number; etc.) may be stored on the card.

The preferred security system of the invention utilizes the identification method and apparatus and generally further comprises a camera means, a card accepting means which causes a user to substantially assume a particular position relative to the camera, a means for reading information stored on the identification card, and information processing means for comparing information obtained by the camera with information stored on the card. If desired, the identification card apparatus may contain additional information beyond parameter ratios or values, and if so, the system may contain an on-line data base of acceptable or refusable cards based on the additional information (as is typical of "hot-card" systems).

Other objects, features, and advantages of the invention will become apparent to those skilled in the art upon reference to the following detailed description of the invention and the accompanying drawings.

DETAILED DESCRIPTION OF THE PREFERRED EMBODIMENT

Before turning to FIG. 1, it is desirable to provide a basic understanding of the principles of the invention.

People are distinguished by their personal appearance, and in particular by their face details. The human eye is extremely sensitive to minor differences characterizing the smallest face details of other people. In fact, even the identity of one identical twin as opposed to the other twin is discernable to the human eye. This is so because each person's face is unique, even if the differences between two particular people is very small. Because the face of an individual is unique, it is has been determined that facial parameters which uniquely identify an individual and which may be expressed in lengths may be found. In fact, without surgical intervention, these facial parameters and ratios of the same typically remain substantially unchanged from adolescence to the advanced age of human males and females.

In establishing a fool-proof identification system which forces the user of an ID card to be the identical individual who owns the ID card by recording indications of the individual's facial parameters on the ID card, it will be appreciated that two factors are critical in establishing identity. First, the facial points or locations which define the facial parameters must be identifiable and measurable by the system which receives the ID card. For example, point locations which are particularly identifiable by optical scanners are points which upon scanning will appear uniformly black surrounded by white, or vice versa. Second, the facial points or locations should not be coverable by haircut style, beard, moustache, or cosmetic makeup. A third factor which is important, as will be discussed hereinafter, is that the points be measurable even if the head is slightly tilted or turned.

Figure 1A:
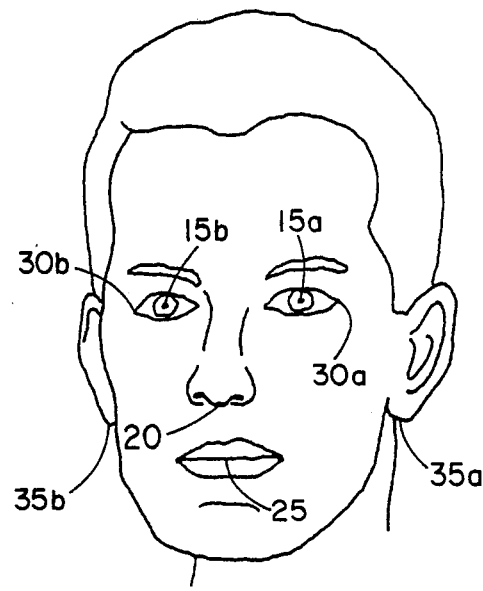
FIGS. 1a and 1b are frontal and profile views respectively of a sketch of a human face nand illustrate discernable point locations required for obtaining facial parameters.

Thus, turning to FIG. 1a, frontal view of a human face 10 is seen. (For purposes of this application, the term "face" is intended to include the ears.) The frontal orientation is defined by the line perpendicular to the imaginary axis passing through the person's ears. Preferably, the frontal view is taken at a slightly upward angle. As indicated in FIG. 1a, in the frontal view the identifiable points or locations would include the middle of the individual's eye retinae 15a and 15b, the nose bottom 20 (which may be defined as the center between the centers of gravity of the nostril openings), the center of the mouth 25 (which may be defined as the point defined by the intersection of the shaded bottom part of the top lip and a line perpendicular to the line connecting the centers of gravity of the nostrils and passing through the nose bottom), the left edge of the left eyeball 30a, and the right edge of the right eyeball 30b, and the tips of the ear lobes 35a and 35b. If desired additional points such as the other edges of the eyeballs, the edges of the mouth (which could be used to define lip width and length), and the centers of gravity of each nostril opening.

Figure 2A:
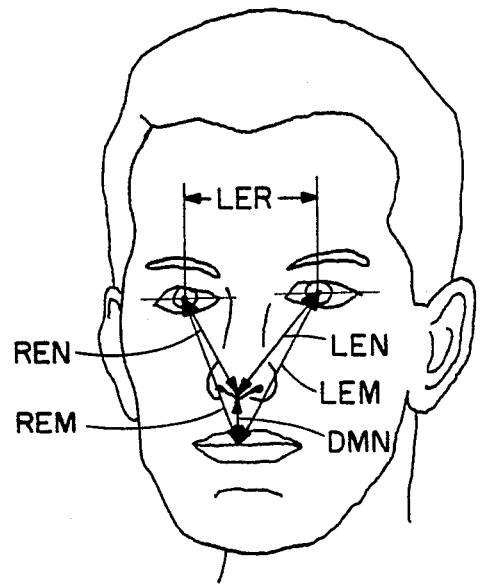
FIGS. 2a and 2b are frontal and profile point locations respectively obtained from FIGS. 1a and 1b which set forth preferred facial parameters.

Using the identifiable points taken from the frontal view, various facial parameters may be defined. (For purposes herein, the terms "facial parameter" and "facial parameter length" are both intended to mean a length between identifiable locations on the face). As indicated in FIG. 2a, the parameters of choice are the distance (LER) between eye retina centers; the distance (LEM) between the left eye retina center and the mouth center; the distance (LEN) between the left eye retina center and the nose bottom; the distance (REM) between the right eye retina center and the mouth center; the distance (REN) between the right eye retina center and the nose bottom, and the distance (DMN) between the mouth center and the nose bottom. These parameters are the preferred parameters due to the fact that hairstyle, makeup, jewelry (e.g. earrings), and facial hair will not hinder determination of these parameters. Of course, if desired, many other facial parameters (distances) could be defined. Indeed, for n identifiable points, there are n−1 factorial possible parameters. Also, if desired, fewer parameters could be used while still identifying an individual with great reliability.

Figure 1B:
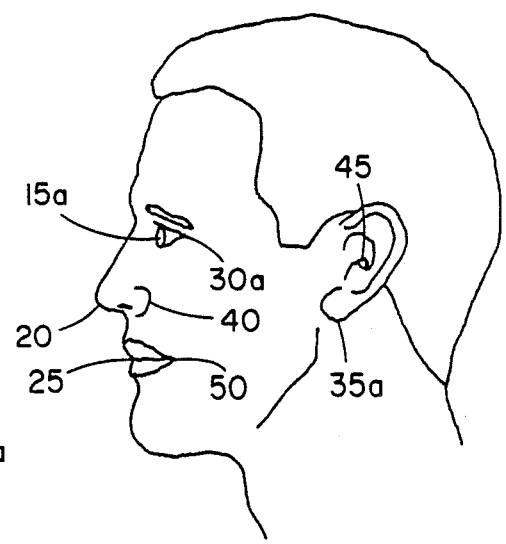

Turning to FIG. 1b, it will be appreciated that at least one additional identifiable point is suggested in a profile view of the individual. Thus, besides the eye retina center 15, the nose bottom 20, the mouth center 25, the eye globe 30, and ear tip 35, the nose root 40 is identifiable. Also, the ear center 45 and mouth edge 50 may be defined and identified.

Figure 2B:
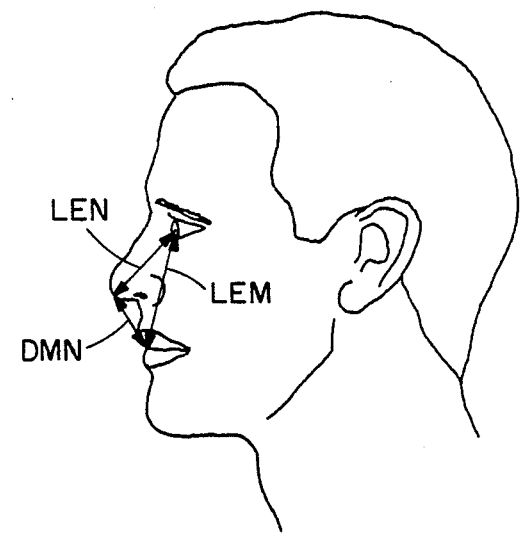

From the various points identified in FIG. 1b, numerous parameters may be derived for the profile view(s) of the individual. As indicated in FIG. 2b, the preferred parameters are the parameters which are above-described in FIG. 2a with respect to the frontal view.

Using the six preferred parameters, up to thirty different parameter ratios (fifteen being the inverse of the other fifteen) may be determined. The primary reason for obtaining the ratio of parameters is that the ratio of parameters is constant regardless of the distance from the individual at which the optical scanner obtains its information. Thus, if parameter ratios are utilized (as opposed to actual lengths), it is not critical to have the original image made at a particular distance from the individual, nor is it critical to have to ID card user be located an exact distance away from the optical scanner which will be used to obtain the parameter information upon use of the credit card. Of course, as aforementioned, facial parameter lengths can be used in making an identification determination. However, if actual lengths are used, a distance determination from the ID card user to the optical scanner location must be made. Those skilled in the art will appreciate the various manners of obtaining the same.

The preferred ratios for establishing identity are: LEN/LER; LEM/LER; REN/LER; REM/LER; and DMN/LER. Of course, other ratios, and/or lengths could also be determined for increased accuracy. Indeed, if desired, ratio averages such as (LEN/LER+REN/LER)/2 and (LEM/LER+REM/LER)/2 may be used instead of or in addition to the parameter ratios, and for purposes herein, averages of ratios shall be considered as being parameter ratios. With the above-listed preferred ratios and ratio averages (AVE 1 and AVE 2) the following chart shows the differnces in the ratios for a random group of people subjected to testing in accord with the system.

| Person | LEN/LER | LEM/LER | REN/LER | REM/LER | DMN/LER | AVE1 | AVE2 |
| --- | --- | --- | --- | --- | --- | --- | --- |
| FG | .763 | 1.087 | .732 | 1.155 | .403 | .748 | 1.121 |
| STY | .926 | 1.222 | .888 | 1.132 | .411 | .907 | 1.177 |
| YB | .840 | 1.391 | .810 | 1.285 | .389 | .825 | 1.338 |
| GB | .862 | 1.111 | .924 | 1.041 | .453 | .893 | 1.076 |
| YM/1 | .793 | 1.107 | .889 | 1.195 | .361 | .841 | 1.151 |
| YM/2 | .794 | 1.108 | .889 | 1.196 | .363 | .8415 | 1.152 |
| PT/1 | .770 | 1.143 | .801 | 1.152 | .427 | .785 | 1.148 |
| PT/2 | .771 | 1.141 | .803 | 1.152 | .425 | .787 | 1.146 |
| TS | .878 | 1.175 | .901 | 1.203 | .330 | .890 | 1.189 |
| YK | .804 | 1.200 | .785 | 1.174 | .470 | .795 | 1.187 |
| RF | .784 | 1.088 | .731 | 1.051 | .373 | .7575 | 1.070 |

From the above chart it is seen that with generally primitive imaging and measurement equipment, the repeatability of the measurements (as shown for PT and YM) was excellent. Indeed such excellent repeatability was obtained without requiring that the tested individual assume a particular alignment or position, except that the person insert a card into a slot of a machine. It is also seen with regard to the above chart that the seven ratios vary by 21% or more from the smallest to the largest ratio of the nine sampled individuals. Indeed, one of the ratios varied over 42% from one individual to another. Moreover, a different set of experiments conducted on "identical" twins showed that discernable differences of more than 3% were found for all seven ratios. Thus, using the six preferred parameters and computing seven preferred parameter ratios (including two ratio averages) therefrom, it will be appreciated that it is extraordinarily unlikely that any two individuals will have all computed parameter ratios being within 2% (typical system accuracy being ±1%) of each other. However, if desired, in order to guard against even this possibility, a security system may be provided with second-tier identification algorithms as will be discussed hereinafter.

Figure 3:
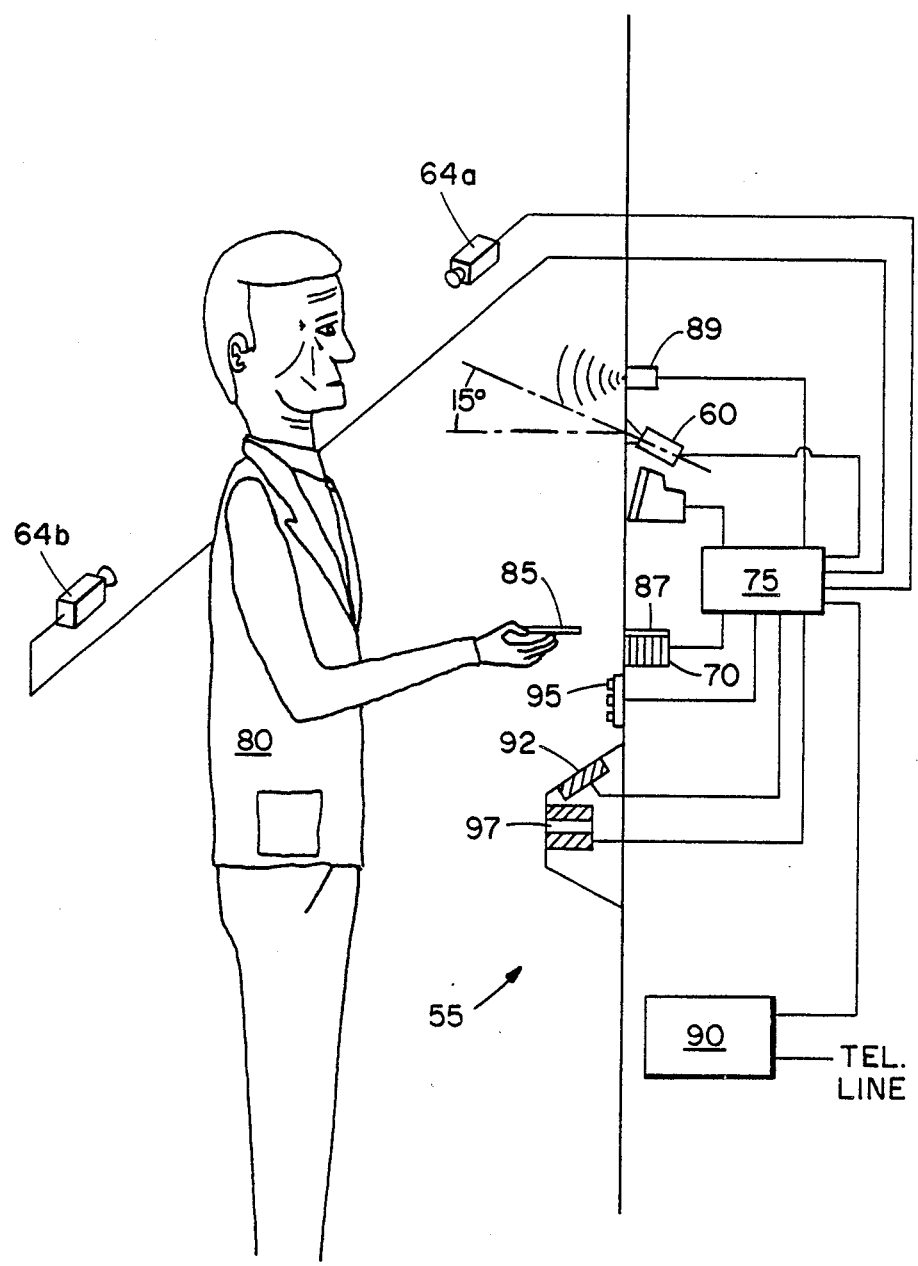
FIG. 3 is a partial schematic of the security system invention using the identification card invention.

Turning to FIG. 3, the preferred security system 55 of the invention is seen. The security system 55 preferably includes front camera 60, side cameras 64a and 64b (if desired), a card accepting and reading means 70 for reading information stored on an identification card, and information processing means 75 for comparing information obtained by the camera with information stored on the card. Typically, the card accepting and reading means 70 is one unit as is known in the art.

The preferred camera 60 is a CCD (coupled charged device) type video camera which can provide an accuracy to at least 0.01 inches. A timing device (clocking section of a processor) which may be part of the information processing means 75 scans each CCD at a predetermined interval. The predetermined interval is set by the total preferred scanning time and by the number and arrangement of the CCD sensors of the camera. Thus, if a preferred frame is scanned in 0.05 seconds, and the CCD video camera is arranged with a grid of CCDs with m CCDs in a row (x axis), and with n (y axis) columns, the total scanning interval (SI) per CCD is set at:

$$SI = 0.05/((n \cdot m) + m)$$

where the scanning is made row by row with each successive row being scanned in an opposite direction, and where the movement of the scanning beam one row lower takes one CCD scanning time interval. It will therefore be recognized that each location in the grid correlates exactly to a point in time for a particular scan.

The provided camera 60 typically includes an electronic filter such that a signal corresponding to a particular CCD will occur only if that CCD sees a light intensity exceeding a certain level. A digital (binary) signal stream is then received by the processor from the CCD grid with a zero indicating low light intensity, and a one indicating intensity above a certain level. If desired, polarized or infrared light can be used to wash the face of the individual desiring access to a system in order to alleviate difficulties which might result due to different skin pigmentation of different humans. With such a "wash", the shadows on the face of the individual (as well as the retinae and dark hair) will then receive a zero values while the remainder of the face will receive "one" values. It will therefore be recognized why the nose bottom and mouth center were defined above as they were, as the nostril shadows and the shadow made by the upper lip (or the space between the lips) will provide a "zero" signal. Because only the shadows and retinae are of interest, only the zero values are analyzed for their time "location".

The location of the dark or shadowed areas of the face of the individual are uniquely determined, because as indicated above, the processor receives both the binary data stream as well as a concurrent clock signal. Because the processor can be arranged to look for definable points according to certain criteria (e.g. the eye retina should be almost exactly round, of a certain size range, and found in the upper half of the head, etc.), only those CCD values which help determine those points need be stored. From the stored values (each covertible into an x-y coordinate), the exact locations of the definable points are identifiable, and middle points (such as between the centers of gravity of the nostril openings), distances, and ratios (including ratio averages) are easily calculated therefrom.

Returning to FIG. 3, during a transaction, a user 80 inserts a card 85 which contains the facial parameter identification information into the slot 87 of the card accepting and reading means 70. The slot 87 is preferably located at a height of approximately forty-eight inches from the ground, while the frontal camera 60 is located behind shatter-proof glass or the like at a height just slightly above the slot (preferably such that the frontal picture is taken upwards at an angle of fifteen to twenty-five degrees). Because some dexterity is required to insert the card 85 into slot 87, the user must focus his or her eyes on the slot 87. Therefore, the user's head will typically bend forward slightly and angle downward slightly with the eyes focussed in a forward direction. Because of this, the user will most always assume a position where the head is within plus or minus ten degrees (and typically plus or minus five degrees) of a direct frontal position. With such a permitted range, the measured parameter accuracy will be accurate to a deviation of approximately ±1.5% as the measuring mistake is proportional to the cosine of ten degrees which equals 0.9848078. With a parameter accuracy of ±1.5%, the parameter ratio may deviate as much as ±3% (1.01519/0.98481 = 1.03085), if the parameters of the ratio each deviate by their maximum in different directions. However, this deviation may be reduced to an expected accuracy of approximately ±2% by normalization. Thus, by calculating the eye retinae distance (LER) as obtained, and comparing the value to the expected LER value, a determination of angle can be had. From the angle determination, normalization of the other parameters can be conducted. It is also of note that if the head is located plus or minus five degrees from a direct frontal position, the parameter accuracy will be within ±0.5%, and the parameter ratio will only deviate as much as ±1%.

While the user 80 inserts the card, frontal camera 60 (which is preferably the same model as was used to obtain the information which was stored on card 85) may be scanning the face of the user. In addition, if desired, side (profile) cameras 64a and 64b may be provided to scan the face (profile) of the user. Or, if desired, instead of the profile cameras, mirrors and/or prisms may be arranged such that the frontal camera 60 may be scanned a second time to provide the profile information. Further, sonic or other means 89 may be provided so that determination of the distance between the user's face and the cameras may be had. The information obtained by the cameras (and sonic means 89) is sent to information processing means 75 where it is processed and compared with the information read from the card 85 by the card accepting and reading means 70. If the information compares favorably, identification is established, and the transaction may occur. If the information does not compare favorably, the user may be requested to reinsert the card and attempt again. If the information still does not compare favorably, the card number may be recorded by the reading means 70 such that notification of improper usage may be made.

It will be appreciated that depending on the level of security desired, and the nature of card 85, the security system 55 may be altered accordingly. Thus, card 85 may include not only facial parameter information, but other identification information such as a Social Security number, signature information, a card number, a driving license number, etc. If card 85 does include a card number, or a Social Security number, security system 55 may be provided with means 90 for obtaining and/or storing "hot card" data from a central data bank, or for storing a list of authorized user numbers. Thus, upon insertion of the card 85 into slot 87, a check of the card by card number would be made by comparing the card number to the data in data storage means 90. If the card was acceptable, the identification procedure would then continue. By hard-wiring the data storage means 90 to the central data bank, or via the use of telecommunications, the "hot card" or authorized user list could be updated regularly. Of course, even if the updating system was "down", the identification procedure could still be carried out effectively. Thus, it will be appreciated that the provided system can still conduct a transaction in an "off-line" mode.

For an even more secure arrangement, the user 80 could be asked to supply his signature on signature reading means 92. Then, according to techniques known in the art as described in the patents listed in the Background section herein, a comparison of the signature read by reading means 92 and the signature information stored on card 85 may be had. Other secondary identification algorithms might include fingerprint comparison (as disclosed in others of the patents listed in the Background section herein), and personal information comparison, such as providing a mother's maiden name, a birthdate, a code number, or other such information. Of course, for a personal information comparison, interactive means such as a computer screen and keyboard 95 should be provided, while for a fingerprint comparison optical pad means 97 would be provided.

It will be appreciated that depending on the type of identification card utilized (e.g. bar coded, magnetic coded, optical or chip memories, punched card, etc.), different amounts of data storage (memory) will be available. However, even with minimal amounts of memory available (e.g. thirty-two bits) as may be found in the most primitive of memory cards, an identification method utilizing at least five facial parameters ratios will be available as each parameter ratio may be stored in only four bits (for a total of twenty bits). With four bits per ratio, sixteen different ratio ranges may be identified for each parameter ratio. Assuming a uniform distribution, the likelihood of a particular individual having the same five facial parameter ratio values as another particular individual would be one in sixteen to the fifth power, or less than one in a million. To reduce even that possibility, actual parameter values or additional ratios could be stored in the remaining twelve bits. Or, if desired, an identification code number, or other information could be stored in the twelve remaining bits. Further, if desired, instead of four bits being used to define a ratio, five or six bits could be used for one or more of the ratios, particularly if certain ratios are susceptible to wide ranges.

It should be appreciated that if an optical card or a card with a chip embedded in the card are used, much more data can be stored. Thus, not only may a tremendous amount of identification data (e.g. facial parameter values, facial parameter ratios, secondary identification information such as handwriting information and/or fingerprint information and/or personal information and/or code numbers, full facial picture, full or partial head picture) be stored, but other information such as a driver license number, Social Security number etc. may be stored. Further, if desired, commercial transaction information may be stored on the card such as transaction date, transaction type (debit or credit), transaction location, merchant code, amount, merchandise code, etc. Likewise, the card could be used as a credit or debit card. With an optical card, approximately ten thousand complete records of transactions could be recorded and stored.

With regard to the card 85 of the invention, its only required capability is that it be capable of storing facial parameter ratio information in such a manner such that the information may be read (preferably by machine). The card 85, however, may also have printed information thereon either under a laminated layer or in an embossed form. The printed information may include: the type and name of card, a service mark emblem; the issuer's name; an account number; the cardholder's name; and an expiration date. If desired, a picture of the cardholder may be included such that in transactions involving a merchant, the merchant can visually compare the user's appearance to the card picture.

Figure 4A:
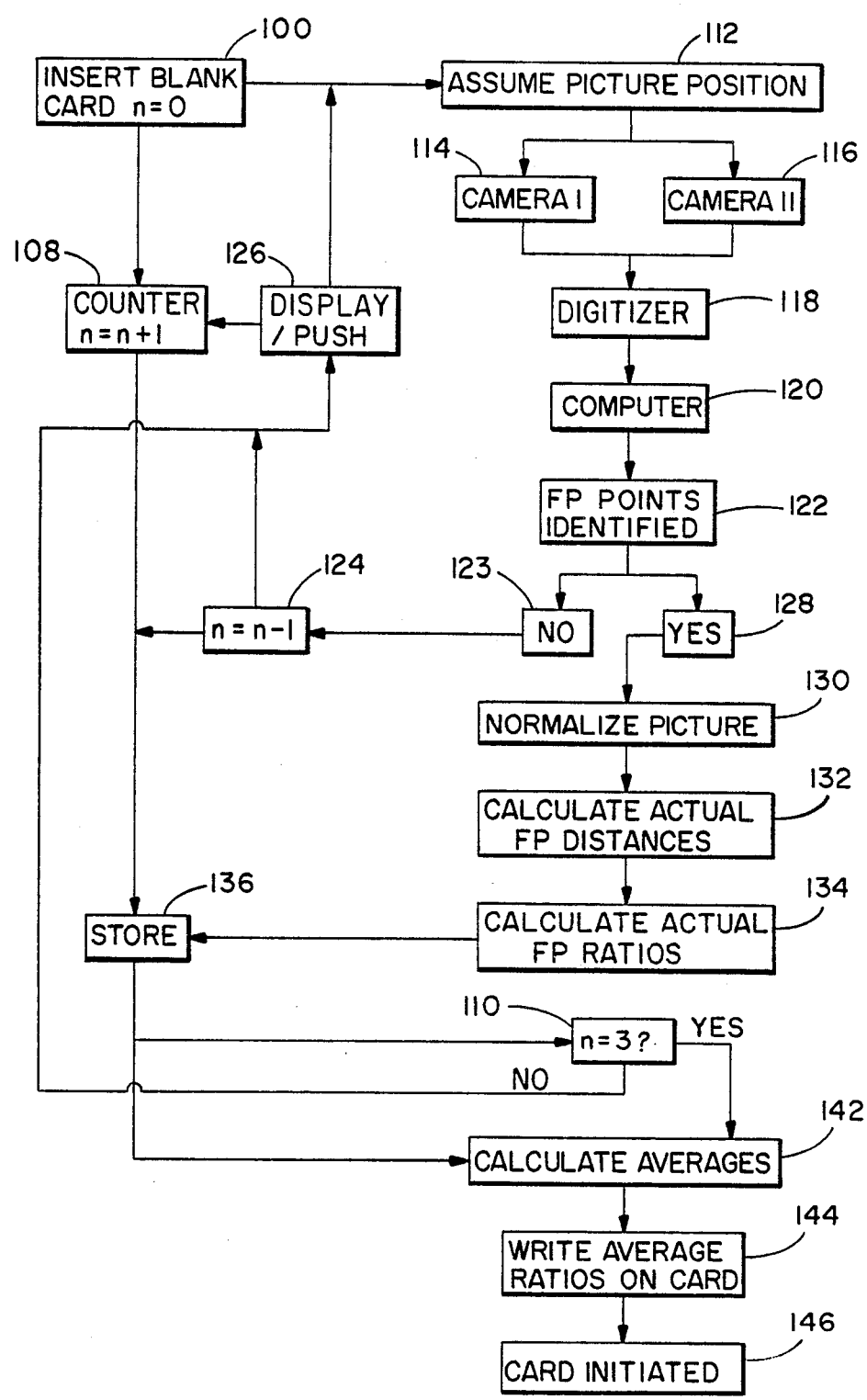
FIGS. 4a and 4b are flow charts of the preferred algorithms used by the security system of FIG. 3 for initializing the security card apparatus, and for establishing identification during a transaction.

Turning to FIG. 4a, a flow chart is seen of the preferred algorithm for initializing the card 85 of the invention. Thus, upon presenting proof of identity and other necessary information to satisfy the issuer of identity and worthiness, the individual is asked to insert at 100 a blank card into a slot of a card accepting means. Because it is preferable to obtain a few sets of information, a counter is set to zero at 100 and updated at 108. The counter is compared at 110 to the value three (or any other value representing the desired number of passes). If the counter has reached a value of three, no additional information is required and parameter and ratio determinations may be calculated as described below. Otherwise, (the no branch), information is obtained. Thus, while the count is being determined, the individual is already inserting the card into the card accepting means which is arranged to be substantially identical to the card accepting means of the security systems in which it is to be later used. Upon insertion, the individual assumes a "picture position" as indicated at 112, and frontal and profile pictures are taken as indicated at 114 and 116 by cameras which are arranged to be substantially identical to the cameras of the security systems. If desired, the individual may be instructed to keep his or her head at a desired angle and tilt. The information received from the cameras is digitized at 118 and processe at 120 so that identifiable facial points are found at 122. If any of the points cannot be found as indicated at 123, the count value set at 108 is decreased by one at 124, and at 126 a display instructs the individual to push a special button. The effect of the display causes the individual to focus his eyes and assume the correct picture position. Thus, the routine returns to step 112, and simultaneously updates the counter once again at 108.

If the facial points can be found as indicated at 128, the facial parameter distances are calculated at 132 and stored. If desired, prior to calculating the parameter distances, the vertical and horizontal frame of the digital "picture" may be normalized at 130. From the parameter distances, the desired facial parameter ratio information is calculated at 134 and stored at 136. If the stored values are the first or second set of values calculated for the individual as determined at 110, the individual is instructed at 126 by the display to push the special button or to reinsert the card. Upon the third set of values being calculated and stored at 136, the average of each of the ratios and any parameter distances are calculated at 142. The average of all of the ratios and/or parameter values are then written onto the card at 144 in the desired fashion (e.g. optically, magnetically, etc.) Further, if desired, secondary identification information may be obtained, coded, and stored on the card. The card is thus deemed to be initialized at 146, and only at this point can it be used in the provided security system.

Figure 4B:
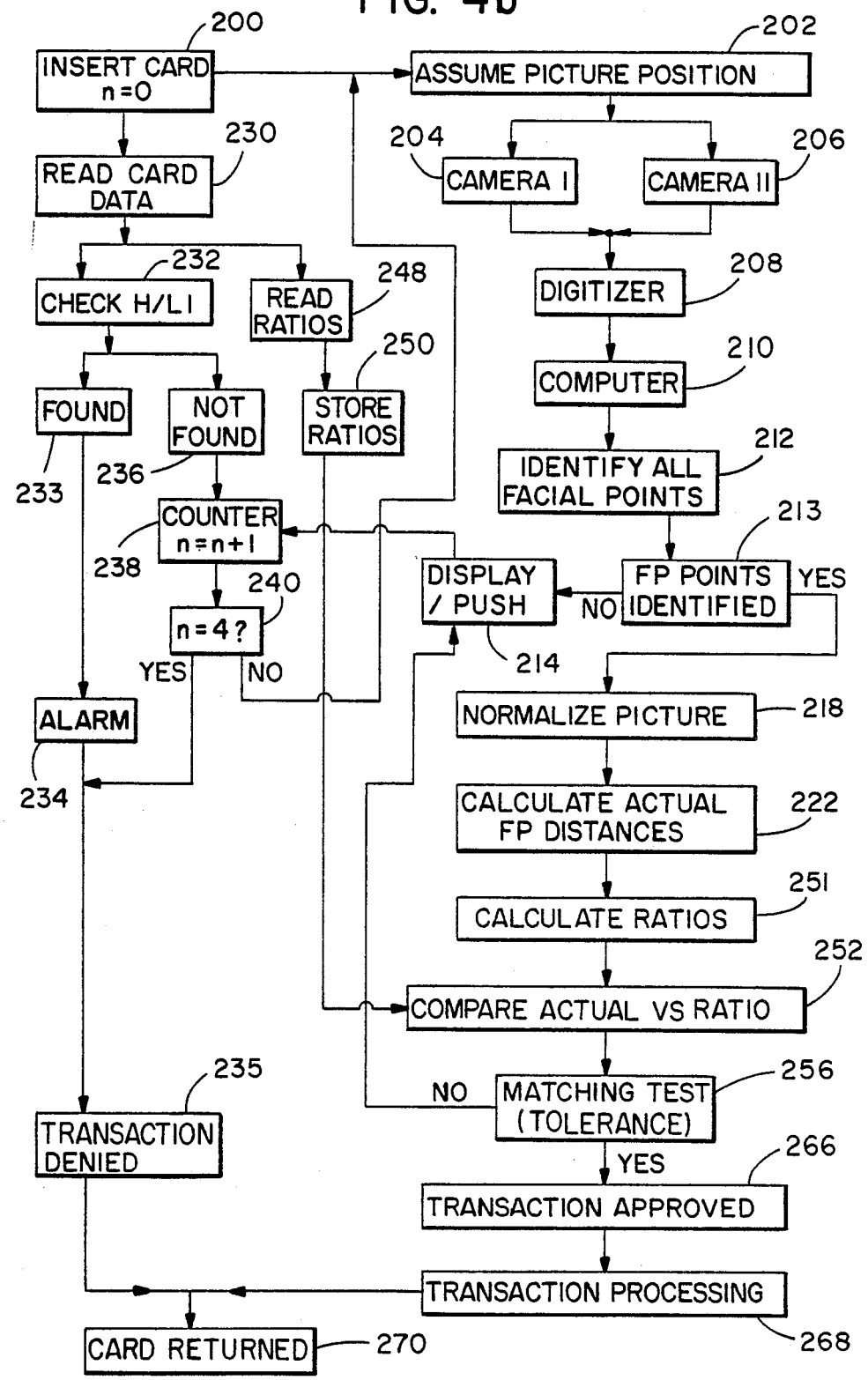

After the card has been arranged, the individual may use the card by inserting the card into a card reader at 200 as seen in FIG. 4b. The actual action of inserting the card at 200 establishes the position of the individual as indicated at 202 and as aforedescribed. As the card is inserted into the card reader, a frontal camera and, if desired, at least one side camera are activated and scan the face of the individual as indicated at 204 and 206. The information so obtained in digitized at 208 and fed into a computer at 210. The computer is programmed to analyze the digitized data for identifiable points or locations on the face of the individual. After locating the identifiable points at 212, the computer can then compute the plurality of distances between the points if all of the points are identified. However, if at 213 all of the facial points are for some reason not identified, the computer steps out of the program at 214 and directs a display screen to request that the user press a particular buton or reinsert the card. If the facial parameters are identified, the program continues at 218 by normalizing, (e.g. for distance and/or for face angle and/or for the horizontal and vertical frames of the scanned information) if desired or required. Then, at 222 the distances between the identified points are then calculated for the desired facial parameters. Thus, with the distance (parameters) determined, the data is available for a comparison as will be described hereinafter between the computed parameters and those stored on the card.

In parallel with steps 204 through 222, where data is collected so that the facial parameters of the individual using the card may be calculated, the card is read at 230 by the card reader. If desired, a first screening may occur at this point, as data on the card such as card number may be compared at 232 with a "hot card" list to determine whether the card should be given access to the system. If the card is "hot" as determined at 233, an alarm is sounded at 234 and the transaction is denied at 235. If desired, in the case of the "hot card", the card may be retained by the machine. If the card passes the first screening, as indicated at 236, the program updates at 238 and checks at 240 the number of times that the card has been inserted for the same transaction. If the card is determined at 240 to have been inserted three or less times for the same transaction, then the facial parameter distance information and the facial parameter ratio information stored on the card is read at 248 and 250. Otherwise, the transaction is denied at 235 and the card is returned at 270. If desired, a record of the denied transaction can be locally stored in the system and/or forwarded to a central computer for notification of a possible hot card.

With a first screening having been accomplished and the information on the card having been read, and with information regarding the card user having been obtained, the desired facial parameter ratios may be calculated at 251. Then the facial parameter ratios recorded on the card and obtained by the system may be compared at 252. Likewise, facial parameter values may also be compared, provided the distance of the user relative to the camera is known. If all of the comparisons indicate a match of values within a selected tolerance, a "match" determination is made at 256, and the program continues with a transaction approval at 266 and transaction processing at 268. The card is then returned at 270. If a match is not made at 256, the user is directed at 214 by a display to push a particular button. By causing the user to push the button, the user is forced to assume picture position and the procedure continues at step 202. Simultaneously, the attempt (n) value is updated at 238 and compared at 240 to determine whether the number of attempts at the same transaction has exceeded the predetermined threshold value.

There has been described and illustrated herein a fully secure apparatus and method for positively and uniquely identifying an individual, and a security system utilizing the identification apparatus and method. While particular embodiments of the invention have been described, it is not intended that the invention be limted thereby, as it is intended that the invention be broad in scope and the specifications be read likewise. Thus, while a preferred algorithm for identification was set forth, the algorithm may be changed and refined in many ways. For example, while facial parameter ratios are preferably compared, the invention also encompasses comparing only facial parameter distances (preferably normalizing the results for distance via use of sonic or other distance locating means), or comparing para eter distances as well as ratios. Likewise, the invention encompasses a comparison of a ratio of two first parameter distances with a ratio to two second parameter distances, such that identity will be established if the ratio values are substantially equal. Moreover, the criteria for determining that a "match" has been found may be set according to various requirements. Thus, for example, depending on the level of security desired, the storage capacity of the card, and the accuracy of the system provided, a "match" may be determined to have been found if the total additive difference of five particular ratios is less than six percent, provided no one ratio differs by more than three percent. Of course, other criteria could be used.

While particular "facial parameters", and "facial parameter ratios" were described as being preferred for determining an individual's identity, those skilled in the arts will recognize that depending upon the desired accuracy of the system, fewer or more parameters and parameter ratios, as well as different parameters and parameter ratios could be utilized. Likewise, while discussion was had with regard to obtaining facial parameter information from a frontal view and a profile view, it will be appreciated that information could also be gleaned from an angled view. Also, while the storing of bit code corresponding to ratio and parameter values was discussed, indications of values may be obtained and stored in many ways. For example, the information storage means on the identification card could range, e.g., from a laminated magnetic strip, to an embedded integrated circuit, to hole punched in the card itself. Further yet, it will be appreciated that the provided system equipment could vary greatly, as different types of cameras could be used, a timing technique for determining locations need not be used, and the processor used for calculations and timing could take many forms. Therefore, it will be apparent to those skilled in the art that many other changes and modifications may be made to the invention as described in the specification without departing from the spirit and scope of the invention as so claimed.

I claim:

1. A method for determining whether a person presenting an identification card which has stored thereon an indication of at least one ratio of at least a first and second facial parameter of an individual, is the individual whose facial parameter ratio indication is stored on said card, said first facial parameter comprising the distance from a first identifiable location to a second identifiable location on said individual's head, and said second facial parameter comprising the distance from a third identifiable location on said individual's head to one of said first, said second, and a fourth identifiable location on said individual's head, said method comprising:

(a) obtaining an indication of at least the value of one ratio of first and second facial parameters of said person presenting said identification card, said obtained indication corresponding to at least said indication of said ratio stored on said identification card; and (b) comparing the indication of the value of said stored ratio with the indication of the value of said ratio obtained of said person presenting said card.

2. A method according to claim 1, wherein:

said first and second identifiable locations are the centers of the retinae of the individual.

3. A method according to claim 2, wherein:
said at least first and second facial parameters includes at least the distance between eye retina centers, and the distance between one of the right eye and left eye retina centers and the nose bottom, and
said at least one ratio includes the ratio between the distance between the eye retina centers, and the distance between one of the right eye and left eye retina centers and the nose bottom.

4. A method according to claim 2, wherein:
said at least first and second facial parameters comprises six facial parameters including the distance between eye retina centers, the distance between the left eye retina center and the mouth center, the distance between the left eye retina center and the nose bottom, the distance between the right eye retina center and the mouth center, the distance between the right eye retina center and the nose bottom, and the distance between the mouth center and the nose bottom.

5. A method according to claim 4, wherein:
said at least one facial parameter ratio comprises
the ratio between the distance between the eye retina centers and the distance between the right eye retina center and the mouth center,
The ratio between the distance between the eye retina centers and the distance between the left eye retina center and the mouth center,
the ratio between the distance between the eye retina centers and the distance the left eye retina center and the nose bottom,
the ratio between the distance between the eye retina centers and the distance the right eye retina center and the nose bottom, and
the ratio between the distance between the eye retina centers and the distance betweeen the mouth center and the nose bottom.

6. A method according to claim 1, wherein:
said at least one stored ratio of facial parameters of said individual is obtained from at least a frontal scan of said individual, and said at least one ratio of parameters obtained of said person presenting said card is obtained from at least a frontal scan of said person.

7. A method according to claim 6, wherein:
said frontal scans of said individual and said person are taken at an upwards angle.

8. A method according to claim 1, wherein:
said at least one stored ratio of facial parameters of said individual is obtained from at least a scan of the profile of said individual, and said at least one ratio of parameters obtained of said person presenting said card is obtained from at least a scan of the profile of said person.

9. A method according to claim 1, wherein said identification card contains at least one facial parameter length of said individual, further comprising:
(c) obtaining an indication of at least one facial parameter length of said person presenting said identification card, said obtained indication corresponding to at least said indication of said length stored on said identification card; and
(d) comparing the indication of the value of said stored length with the indication of the value of said length obtained from a scan of said person presenting said card.

10. A method according to claim 9, further comprising: (e) prior to step (d), normalizing one of said indication of the value of said stored length and said indication of the value of said length obtained from a scan prior to comparing said indications.

11. A method according to claim 10, where said card further includes an indication of the distance at which the camera which was used to obtain said at least one parameter length was located relative to said invididual upon obtaining said parameter length, wherein:
said normalizing step includes determining the distance between a camera used in said obtaining step (c) and said person presenting said identification card.

12. A method accordin to claim 10, wherein
said normalizing step includes taking a ratio of a first facial parameter length of said individual and said person, and using said ratio as a normalizing factor.

13. A method according to claim 9, wherein, said at least one facial parameter length of said individual comprises at least two facial parameter lengths, and said obtained indications of said person comprises at least two facial parameter lengths, wherein:
said comparing of step (d) comprises
taking the ratio of the corresponding first facial parameter lengths of said individual and said person,
taking the ratio of the corresponding second facial parameter lengths of said individual and said person,
comparing said taken ratios, and
establishing identification if said ratios are substantially identical.

14. A method according to claim 1, wherein said identification card includes indications of additional identification information regarding said individual other than facial parameter ratios and facial parameter lengths, further comprising:
(c) obtaining from said person presenting said identification card information corresponding to said additional identification information on said card; and
(d) comparing indications of the information obtained in step (c) with the indications of said additional identification information on said card.

15. A method according to claim 14, wherein:
said additional identification information includes at least one of a group consisting of code number information, written signature information, and voice signature information.

16. A method for determining whether a person presenting an identification card which has stored thereon an indication of at least one facial parameter length of an individual, is the individual whose facial parameter length is stored on said card, said facial parameter length comprising the distance from a first identifiable location to a second identifiable location on said individual's head, said method comprising:
(a) obtaining an indication of at least the value of one facial parameter length of said person presenting said identification card, said obtained indication corresponding to at least said indication of said facial parameter length stored on said identification card; and
(b) comparing the indication of the value of said stored facial parameter length with the indication of the value of said facial parameter length obtained of said person presenting said card, wherein said first and second identifiable locations are the centers of the retinae of the individual.

17. A method according to claim 16, further comprising:
(c) normalizing, prior to comparing said indications, one of said indication of the value of said stored length and said indication of the value of said length obtained from a scan.

18. A method according to claim 17, where said card further includes an indication of the distance at which a camera which was used to obtain said at least one parameter length was located relative to said individual upon obtaining said parameter length, wherein:
said normalizing step includes determining the distance between a camera used in said obtaining step (b) and said person presenting said identification card.

19. A method according to claim 17, wherein
said normalizing step includes taking a ratio of corresponding first facial parameter lengths of said individual and said person, and using said ratio as a normalizing factor.

20. A method according to claim 16, wherein, said at least one facial parameter length of said individual comprises at least two facial parameter lengths, and said obtained indications of said person comprises at least two facial parameter lengths, wherein:
said comparing of step (b) comprises
taking the ratio of the corresponding first facial parameter lengths of said individual and said person,
taking the ratio of the corresponding second facial parameter lengths of said individual and said person,
comparing said taken ratios, and
establishing identification if said ratios are substantially indentical.

21. A method according to claim 16, wherein said identification card includes indications of additional identification information regarding said individual other than facial parameter lengths, further comprising:
(c) obtaining from said person presenting said identification card information corresponding to said additional identification information on said card; and
(d) comparing indications of the information obtained in step (c) with the indications of said additional indentification information on said card.

22. A method according to claim 21, wherein:
said additional identification information includes at least one of a group consisting of facial parameter ratio information, code number information, written signature information, and voice signature information.

23. A method for determining whether a person presenting an identification card which has stored thereon an indication of at least one facial parameter length of an individual, is the individual whose facial parameter length is stored on said card, said facial parameter length comprising the distance from a first identifiable location to a second identifiable location on said individual's head, said method comprising:
(a) obtaining an indication of at least the value of one facial parameter length of said person presenting said identification card, said obtained indication corresponding to at least said indication of said facial parameter length stored on said identification card; and
(b) comparing the indication of the value of said stored facial parameter length with the indication of the value of said facial parameter length obtained of said person presenting said card,
wherein said at least one facial parameter is chosen from a group consisiting of the distance between eye retina centers, the distance between the left eye retina center and the mouth center, the distance between the left eye retina center and the nose bottom, the distance between the right eye retina center and the mouth center, and the distance between the right eye retina center and the nose bottom.

24. A method according to claim 23, further comprising:
(c) normalizing, prior to comparing said indications, one of said indication of the value of said stored length and said indication of the value of said length obtained from a scan.

25. A method according to claim 24, where said card further includes an indication of the distance at which a camera which was used to obtain said at least one parameter length was located relative to said individual upon obtaining said parameter length, wherein:
said normalizing step includes determining the distance between a camera used in said obtaining step (b) and said person presenting said identification card.

26. A method according to claim 24, wherein
said normalizing step includes taking a ratio of corresponding first facial parameter lengths of said individual and said person, and using said ratio as a normalizing factor.

27. A method for identifiying an individual, comprising:
(a) via imaging at least a portion of said individual's head, obtaining an indication of
(1) a ratio of a first and second facial parameter of said individual, said first facial parameter comprising the distance from a first identifiable location to a second indentifiable location on the individual's head, and said second facial parameter comprising the distance from a third ientifiable location on the individual's head to one of said first, said second, and a fourth identifiable location on the individual's head;
(b) storing on a storage medium values indicative of said ratio of said first and second facial parameters of said individual;
(c) upon attempting to identify a person requesting access to a secure system, obtaining an indication of the value of a ratio of first and second facial parameters of said person requesting access corresponding to at least said ratio stored on said storage medium; and
(d) comparing the indications of the value of said stored ratio with the indication of the value of said ratio obtained of said person requesting access.

28. A method for identifying an individual according to claim 27, wherein:
said first and second identifiable locations are the centers of the retinae of the individual.

29. A method for indentifiying an individual according to claim 28, wherein:
said ratio is the ratio between the distance between the eye retina centers and the distance between the right eye retina center and the nose bottom.

30. A method according to claim 28, wherein:

five facial parameter ratios are found including
the ratio between the distance between the eye retina centers and the distance between the right eye retina center and the mouth center,
the ratio between the distance between the eye retina centers and the distance between the left eye retina center and the mouth center,
the ratio between the distance between the eye retina centers and the distance the left eye retina center and the nose bottom,
the ratio between the distance between the eye retina centers and the distance the right eye retina center and the nose bottom, and
the ratio between the distance between the eye retina centers and the distance between the mouth center and the nose bottom.

31. A method according to claim 27, wherein:
said stored ratio of facial parameters of said individual is obtained from at least one frontal scan of said individual, and said ratio of parameters obtained of said person presenting said card is obtained from at least a frontal scan of said person.

32. A method according to claim 31, wherein:
said frontal scans of said individual and said person are taken at an upwards angle.

33. A method according to claim 27, wherein said identification card includes indications of additional identification information regarding said individual other than facial parameter distances and facial parameter ratios, further comprising:
(e) obtaining from said person presenting said identification card information corresponding to said additional identification information on said card; and
(f) comparing indications of the information obtained in step (e) with the indications of said additional identification information on said card.

34. A method according to claim 33, wherein:
said additional identification information includes at least one of a group consisting of code number information, written signature information, and voice signature information.

35. An identification card having indications readable by a card reading means, comprising:
a card capable of insertion into said card reading means, said card including information storage means, said information storage means storing and indication of a ratio of a first and second facial parameter of said individual,
said first facial parameter comprising the distance from a first identifiable location to a second identifiable location on the individual's head, and said second facial parameter comprising the distance from a third identifiable location on the individual's head to one of said first, said second, and a fourth identifiable location on the individual's head.

36. An identification card according to claim 35, wherein:
at least five facial parameter ratios are stored including,
the ratio between the distance between the eye retina centers and the distance between the right eye retina center and the mouth center,
the ratio between the distance between the eye retina centers and the distance between the left eye retina center and the mouth center,
the ratio between the distance between the eye retina centers and the distance the left eye retina center and the nose bottom,
the ratio between the distance between the eye retina centers and the distance the right eye retina center and the nose bottom, and
the ratio between the distance between the eye retina centers and the distance between the mouth center and the nose bottom.

37. An identification card according to claim 35, wherein:
said stored ratio of facial parameters of said individual is obtained from at least a frontal scan of said individual.

38. An identification card according to claim 37, wherein:
said frontal scan of said individual was taken at an upwards angle.

39. An identification card according to claim 35, wherein:
said stored facial parameter of said individual was obtained from at least a frontal scan of said individual.

40. An identification card according to claim 35, wherein:
said information storage means further stores an indication of the distance at which a camera which was used to obtain said parameter distance was located relative to said individual upon obtaining said parameter distance.

41. An identification card according to claim 35, wherein:
said information storage means further stores an indication of additional identification information including at least one of a group consisting of code number information, written signature information, and voice signature information.

42. An identification card according to claim 35, wherein:
said information storage means is one of a magnetic strip laminated onto said card, and an integrated circuit imbedded in said card.

43. An identification card having indications readable by a card reading means, comprising:
a card capable of insertion into said card reading means, said card including information storage means, said information storage means storing an indication of at least a first facial parameter of an individual, said first facial parameter comprising the distance from a first identifiable location to a second identifiable location on the individual's head,
said first and second identifiable locations being the centers of the eye retinae of the individual.

44. Ann identification card according to claim. 43 wherein:
at least six facial parameters are stored including the distance between eye retina centers, the distance between the left eye retina center and the mouth center, the distance between the left eye retina center and the nose bottom, the distance between the right eye retina center and the mouth center, the distance between the right eye retina center and the nose bottom, and the distance between the mouth center and the nose bottom.

45. A security system for determining whether the identity of a person attempting to gain entry to a port with an identification card is the same as the owner of said identification card, said security system comprising:

(a) a card accepting and reading means for accepting and reading an identification card containing indications of
a ratio of a first and second facial parameter of said owner, said first facial parameter comprising the distance from a first identifiable location to a second identifiable location on said owner's head, and said second facial parameter comprising the distance from a third identifiable location on said owner's head to one of said first, said second and a fourth identifiable location on the owner's head;

(b) a camera means for scanning the face of said person inserting said identification card into said card accepting means; and (c) information processing means for obtaining information from said camera means, for processing said obtained information to determine an indication of a ratio of a first and second facial parameter of said person, wherein said facial parameter ratio for said person corresponds to said ratio for said owner, and for comparing said indications obtained and processed by said information processing means to said indication on said card read by said card accepting and reading means.

46. A security system according to claim 45, wherein said identification card includes an identification card number, further comprising:
(d) data base storage means for storing
a first list of card identification numbers barred from said security system,
wherein said card accepting and reading means can read said card identification number, and wherein said information processing means is connected to said data base storage means and is arranged to compare the identification card number of said person with said first list.

47. A security system according to claim 46, further comprising:
(e) data communication means for connecting said data base storage means to a central data base storage means, wherein
said information processing means at least partially obtains said first from said central data base storage means via said data communication means.

48. A security system according to claim 45, further comprising:
(d) illumination means for illuminating the face of said person upon an attempt of said person to gain entry to said port.

49. A security system according to claim 48, wherein: said illumination means includes infrared ray means.

50. A security system according to claim 45, further comprising:
(d) distance determination means for determining the distance between said camera means and said person.

51. A security system according to claim 45, wherein: at least five facial parameter ratios are contained including,
the ratio between the distance between the eye retina centers and the distance between the right eye retina center and the mouth center,
the ratio between the distance between the eye retina centers and the distance between the left eye retina center and the mouth center,
the ratio between the distance between the eye retina centers and the distance the left eye retina center and the nose bottom,
the ratio between the distance between the eye retina centers and the distance the right eye retina center and the nose bottom, and
the ratio between the distance between the eye retina centers and the distance between the mouth center and the nose bottom.

52. A security system according to claim 51, wherein: said camera is further arranged to obtain a profile scan of the face of said person.

53. A security system according to claim 45, wherein: said camera is arranged to obtain a frontal scan of the face of said person.

54. A security system according to claim 53, wherein: said camera is further arranged to obtain said frontal scan at an upwards angle.

55. A security system according to claim 45, wherein said identification card includes an identification card number, further comprising:
(d) data base storage means for storing a list of card identification numbers permitted access to said security system,
wherein said card accepting and reading means can read said card identification number, and wherein said information processing means is connected to said data base storage means and is arranged to compare the identification card number of said person with said list of card identification numbers permitted access to said security system.

56. A security system according to claim 55, further comprising:
(e) data communication means for connecting said data base storage means to a central data base storage means, wherein
said information processing means at least partially obtains said list of card identification number permitted access to said security system from said central data base storage means via said data communication means.

57. A security system for determining whether the identity of a person attempting to gain entry to a port with an identification card is the same as the owner of said identification card, said security system comprising:
(a) a card accepting and reading means for accepting and reading an identification card containing indications of a least a first facial parameter of said owner, said first facial parameter comprising the distance from a first identifiable location to a second identifiable location on said owner's head,
said first and second identifiable locations being the centers of the eye retinae of the owner;
(b) a camera means for scanning the face of said person inserting said identification card into said card accepting means; and
(c) information processing means for obtaining information from said camera means, for processing said obtained information to determine an indication of at least said first facial parameter of said person, wherein said first facial parameter for said person corresponds to said for said owner, and for comparing said indications obtained and processed by said information processing means to said indications on said card read by said card accepting and reading means.

58. A security system according to claim 57, wherein:

at least six facial parameters are contained including the distance between eye retina centers, the distance the eye retina center and the mouth center, the distance between the left eye retina center and the bottom, the distance between the right eye retina center and the mouth center, the distance between the right eye retina center and the nose bottom, and the distance between the mouth center and the nose bottom.

59. A method for identifying an individual, comprising:
(a) via imaging at least a portion of said individual's head, obtaining an indication of a facial parameter distance of said individual;
(b) storing on a storage medium a value indicative of said facial parameter distance;
(c) upon attempting to identify a person requesting access to a secure system, obtaining an indication of a facial parameter distance of said person corrresponding to said facial parameter distance value stored on said storage medium; and
(d) comparing the indication of the value of said stored parameter distance with the parameter distance of said person requesting access, wherein
said facial parameter distance of said individual is the distance between first and second identifiable locations on said individual's head, said first and second identifiable locations being the centers of the retinae of the individual.

60. A method for identifying an individual according to claim 59, wherein:

six facial parameters are obtanined including the distance betweeen eye retina centers, the distance between the left eye retina center and the mouth center, the distance between the left eye retina center and the nose bottom, the distance between the right eye retina center and the mouth center, the distance between the right eye retina center and the nose bottom, and the distance between the mouth center and the nose bottom.

61. A method according to claim 59, further comprising:
(e) prior to step (d), normalizing said indication of the value of said stored parameter distance prior to comparing said indications.

62. A method according to claim 61, where said card further includes an indication of the distance at which the camera which was used to obtain said at least one parameter distance was located relative to said individual upon obtaining said parameter distance, wherein:
said normalizing step includes determining the distance between a camera used in said obtaining step (c) and said person presenting said identification card.

63. A method according to claim 59, wherein, two facial parameter distances of said individual and said person are obtained, wherein:
said comparing of step (d) comprises
taking the ratio of corresponding first facial parameter distances of said individual and said person,
comparing said taken ratios, and
establishing identification if said ratios are substantially identical.

* * * * *